United States Patent [19]

(12) United States Patent
Larouche et al.

(10) Patent No.: US 11,700,992 B2
(45) Date of Patent: Jul. 18, 2023

(54) ENCAPSULATED COMPONENTS OF MEDICAL DEVICES, AND METHODS THEREFOR

(71) Applicant: Boston Scientific Scimed, Inc., Maple Grove, MN (US)

(72) Inventors: Adam Michael Larouche, Bloomington, IN (US); Kirsten Viering, Newton, MA (US); John B. Golden, Norton, MA (US); Scott Kippenbrock, Avon, IN (US); Adam Dills, Bloomington, IN (US); Seth Charles Schneider, Jeffersonville, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 104 days.

(21) Appl. No.: 16/454,224

(22) Filed: Jun. 27, 2019

(65) Prior Publication Data

US 2020/0000314 A1 Jan. 2, 2020

Related U.S. Application Data

(60) Provisional application No. 62/691,045, filed on Jun. 28, 2018.

(51) Int. Cl.
*A61B 1/00* (2006.01)
*A61B 1/05* (2006.01)
*A61B 1/06* (2006.01)

(52) U.S. Cl.
CPC .......... *A61B 1/0008* (2013.01); *A61B 1/0011* (2013.01); *A61B 1/00066* (2013.01);
(Continued)

(58) Field of Classification Search
CPC . A61B 1/0008; A61B 1/00096; A61B 1/0011; A61B 1/00137; A61B 1/00186;
(Continued)

(56) References Cited

U.S. PATENT DOCUMENTS 5,089,895 A * 2/1992 Fraker .............. G08B 13/19619
264/271.1
5,830,401 A * 11/1998 Prichard ........... B29C 45/14467
264/262

(Continued)

FOREIGN PATENT DOCUMENTS

CN 107361731 A 11/2017
CN 206729853 U 12/2017
(Continued)

*Primary Examiner* — Aaron B Fairchild
*Assistant Examiner* — Stephen Floyd London
(74) *Attorney, Agent, or Firm* — Bookoff McAndrews, PLLC

(57) ABSTRACT

A distal end portion of a medical device may comprise an image capturing component; a light source; and an encapsulation having inner surfaces contacting and at least partially encompassing the image capturing component and the light source. A shape of the inner surfaces may be mirror image of a shape of exterior surfaces of the image capturing component and the light source that are contacted by the inner surfaces.

20 Claims, 6 Drawing Sheets

(52) U.S. Cl.
CPC ............ *A61B 1/00096* (2013.01); *A61B 1/05* (2013.01); *A61B 1/0661* (2013.01)

(58) Field of Classification Search
CPC . A61B 1/0661; A61B 1/00101; A61B 1/0615; A61B 1/0676; A61B 1/0089; A61B 1/00135; A61B 1/00142; A61B 1/00177; A61B 1/0684; A61M 25/0009
See application file for complete search history.

(56) References Cited

U.S. PATENT DOCUMENTS

| | | | |
|---|---|---|---|
| 6,456,863 B1* | 9/2002 | Levin | A61B 18/1492 600/374 |
| 6,685,092 B2 | 2/2004 | Patel | |
| 7,157,302 B2 | 1/2007 | Rhodes et al. | |
| 7,369,176 B2 | 5/2008 | Sonnenschein et al. | |
| 2005/0234499 A1* | 10/2005 | Olson | A61M 25/1036 606/192 |
| 2006/0063976 A1 | 3/2006 | Aizenfeld et al. | |
| 2009/0043166 A1* | 2/2009 | Ishii | A61B 1/00179 600/130 |
| 2013/0190561 A1 | 7/2013 | Oskin | |
| 2014/0028924 A1* | 1/2014 | Yamaguchi | G03B 17/565 349/1 |
| 2014/0330081 A1* | 11/2014 | Imai | A61B 1/00101 600/129 |
| 2015/0005580 A1* | 1/2015 | Petersen | A61B 1/05 600/112 |
| 2015/0065797 A1* | 3/2015 | Yamamoto | G02B 23/2476 600/109 |
| 2016/0006908 A1 | 1/2016 | Pan et al. | |
| 2016/0051126 A1 | 2/2016 | Trailer et al. | |
| 2017/0127915 A1* | 5/2017 | Viebach | A61B 1/051 |
| 2017/0245734 A1* | 8/2017 | Kaneko | A61B 1/05 |
| 2020/0008658 A1* | 1/2020 | Hayakawa | A61B 1/00177 |
| 2020/0344386 A1* | 10/2020 | Yamamoto | H01L 27/14625 |
| 2021/0022588 A1* | 1/2021 | Schultheis | G02B 6/0008 |

FOREIGN PATENT DOCUMENTS

| | | | |
|---|---|---|---|
| EP | 1 669 019 A2 | 6/2006 | |
| EP | 3207852 B1 | 6/2016 | |
| JP | 2006174883 A * | 7/2006 | ............... A61B 8/12 |
| JP | 2007-296112 A | 11/2007 | |
| JP | 2012-511357 A | 5/2012 | |
| WO | WO-2010066790 A1 * | 6/2010 | ........... A61B 1/0057 |
| WO | WO-2010129324 A2 * | 11/2010 | ......... A61B 1/00096 |
| WO | 2012/099127 A1 | 1/2012 | |

\* cited by examiner

ENCAPSULATED COMPONENTS OF MEDICAL DEVICES, AND METHODS THEREFOR

CROSS-REFERENCE TO RELATED APPLICATION(S)

This application claims the benefit of priority from U.S. Provisional Application No. 62/691,045, filed on Jun. 28, 2018, which is incorporated by reference herein in its entirety.

TECHNICAL FIELD

The present disclosure relates generally to devices, systems, and methods for encapsulated components of medical devices. More specifically, aspects of the present disclosure pertain to devices, systems, and/or methods for encapsulated distal portions of endoscopes.

BACKGROUND

Endoscopes may include a handle portion, which may be gripped by an operator and may include control elements for functions such as steering, suction, water, air, light, and imaging. An endoscope may also include a portion which may be inserted into a subject. For example, an endoscope may include an elongate tube suitable for insertion into a subject. Such an insertion portion may include one or more lumens. The lumens of an insertable portion of an endoscope may support functions, for example, conveying air, water, suction, electricity, data, light, and/or images. Tools may also be inserted via a working channel of an insertable portion of an endoscope. For example, a tool may be inserted by a port in or near the handle of an endoscope.

An insertable portion of an endoscope may terminate in a distal portion. A distal portion of an endoscope may include outlets for air, water, suction, electricity, data, light, images, and/or working tools from lumen(s) of an endoscope. A distal portion may have narrow manufacturing tolerances. However, because a distal portion of an endoscope may include multiple components, these manufacturing tolerances may be difficult to achieve, particularly in small sizes. Therefore, a need exists for distal portions of endoscopes which are manufactured with efficient techniques and which satisfy the requirements for using an endoscope in a subject.

SUMMARY

Examples of the present disclosure relate to, among other things, devices, systems, and methods for encapsulated components of medical devices, including encapsulated distal portions of endoscopes. Each of the examples disclosed herein may include one or more of the features described in connection with the disclosed examples.

A distal end portion of a medical device may comprise an image capturing component; a light source; and an encapsulation having inner surfaces contacting and at least partially encompassing the image capturing component and the light source. A shape of the inner surfaces may be mirror image of a shape of exterior surfaces of the image capturing component and the light source that are contacted by the inner surfaces.

Any example of the distal end portions described herein may additionally or alternatively include one or more of the features below. The encapsulation may form a liquid tight shell. The encapsulation may include at least one of a lens, a prism, an aperture, a filter, a diffuser, a dispersing light feature, a mirror, a window, a grating, or a collimating light feature, or combinations thereof. The encapsulation may include at least one of a fulcrum, a wedge, a cam, a pin, a notch, a piston, a cylinder, a gear, a rack, a pulley, a socket, or a block and tackle, or combinations thereof. The distal end portion may comprise a circuit board. The inner surfaces of the encapsulation may contact and at least partially encompass the circuit board. A shape of the inner surfaces may be a mirror image of a shape of exterior surfaces of the circuit board. The inner surfaces of the encapsulation may contact at least a side surface of the image capturing component. The inner surfaces of the encapsulation may contact at least a top surface and at least a side surface of the light source. The encapsulation may fill all of a space between the image capturing component and the light source. The inner surfaces of the encapsulation may contact at least a bottom surface of the circuit board. The distal end portion may comprise a layer configured to change opacity or reflectance when an electrical current or voltage is applied to the layer. The encapsulation may be formed of a molded, monolithic material. The distal end portion may comprise a cap portion. The inner surfaces of the encapsulation may contact at least a side surface of the image capturing component. The inner surfaces of the encapsulation may contact at least a top surface and at least a side surface of the light source. The encapsulation may fill all of a space between the image capturing component and the light source. Exterior surfaces of the encapsulation may contact inner surfaces of the cap portion. The encapsulation may include at least one of a ridge and a flange. The ridge or the flange may be shaped so as to mate with the cap portion. A distal exterior surface of the encapsulation may have a rounded shape. The distal exterior surface of the encapsulation may contact inner surfaces of the cap portion. The distal end portion may comprise a connection portion. A shape of exterior surfaces of the connection portion may be a mirror image of a shape of interior surfaces of a receptacle disposed on a distal end portion of a medical device. The encapsulation may be transparent. The encapsulation may be formed of an electrically insulating material.

In another example, a method for forming a distal end portion of a medical device may comprise positioning an image capturing component and a light source in a cavity of a mold and introducing an encapsulating material into the cavity. The introduced encapsulating material may encompass at least a portion of the image capturing component and a portion of the light source. The encapsulating material may be allowed to harden.

Any method described herein may include one or more of the features or steps described below. The cavity may include a negative of at least one of a lens, a prism, an aperture, a filter, a diffuser, a dispersing light feature, a mirror, a window, a grating, or a collimating light feature, or combinations thereof. The cavity may include a negative of at least one of at least one of a fulcrum, a wedge, a cam, a pin, a notch, a piston, a cylinder, a gear, a rack, a pulley, a socket, or a block and tackle, or combinations thereof. A circuit board may be positioned in the cavity. The introduced material may encompass at least a portion of the circuit board. The cavity may include a negative of at least one of a ridge and a flange, wherein the ridge or the flange is shaped so as to mate with a cap portion.

In yet another example, a medical device may comprise a proximal control portion; a distal insertion portion; and a distal end portion. The distal end portion may comprise a component and an encapsulation. The encapsulation may have inner surfaces contacting and at least partially encompassing the component. A shape of the inner surfaces may be a mirror image of a shape of exterior surfaces of the component that are contacted by the inner surfaces.

Any medical device may additionally or alternatively include one or more of the features described below. The encapsulation may form a liquid tight shell. The encapsulation may include at least one of a lens, a prism, an aperture, a filter, a diffuser, a dispersing light feature, a mirror, a window, a grating, or a collimating light feature, or combinations thereof. The encapsulation may include at least one of a fulcrum, a wedge, a cam, a pin, a notch, a piston, a cylinder, a gear, a rack, a pulley, a socket, or a block and tackle, or combinations thereof. The distal end portion may further comprise a cap portion. The inner surfaces of the encapsulation may contact least a top surface and at least a side surface of the component. Exterior surfaces of the encapsulation may contact inner surfaces of the cap portion.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

Distal end portions of endoscopes may include a variety of electronic and other components and may connect to a distal insertion portion of an endoscope. Because the distal end portion may be inserted into a body lumen of a patient, these distal end portions must be sterilizable. These distal end portions may also be subject to tight manufacturing requirements. This disclosure describes, for example, a distal end portion which is encapsulated with a material which both satisfies sterilizing requirements and eases manufacturing of the distal end portion. Such an encapsulated end portion may prevent ingress of fluids or other contaminants, which could potentially damage components of an endoscope or other device, including electronic components of such a device. A distal end portion according to the disclosure herein may also assist in miniaturization by allowing integration of functional components such as optical and mechanical features into an encapsulation. Although endoscopes are referenced herein, reference to endoscopes or endoscopy should not be construed as limiting the possible applications of the disclosed systems. Other applications include, for example, any medical or non-medical device requiring encapsulation of components, particularly small-scale electrical components. Such medical devices include, for example, colonoscopes, ureteroscopes, bronchoscopes, catheters, sheaths, imagers, etc.

Figure 1:
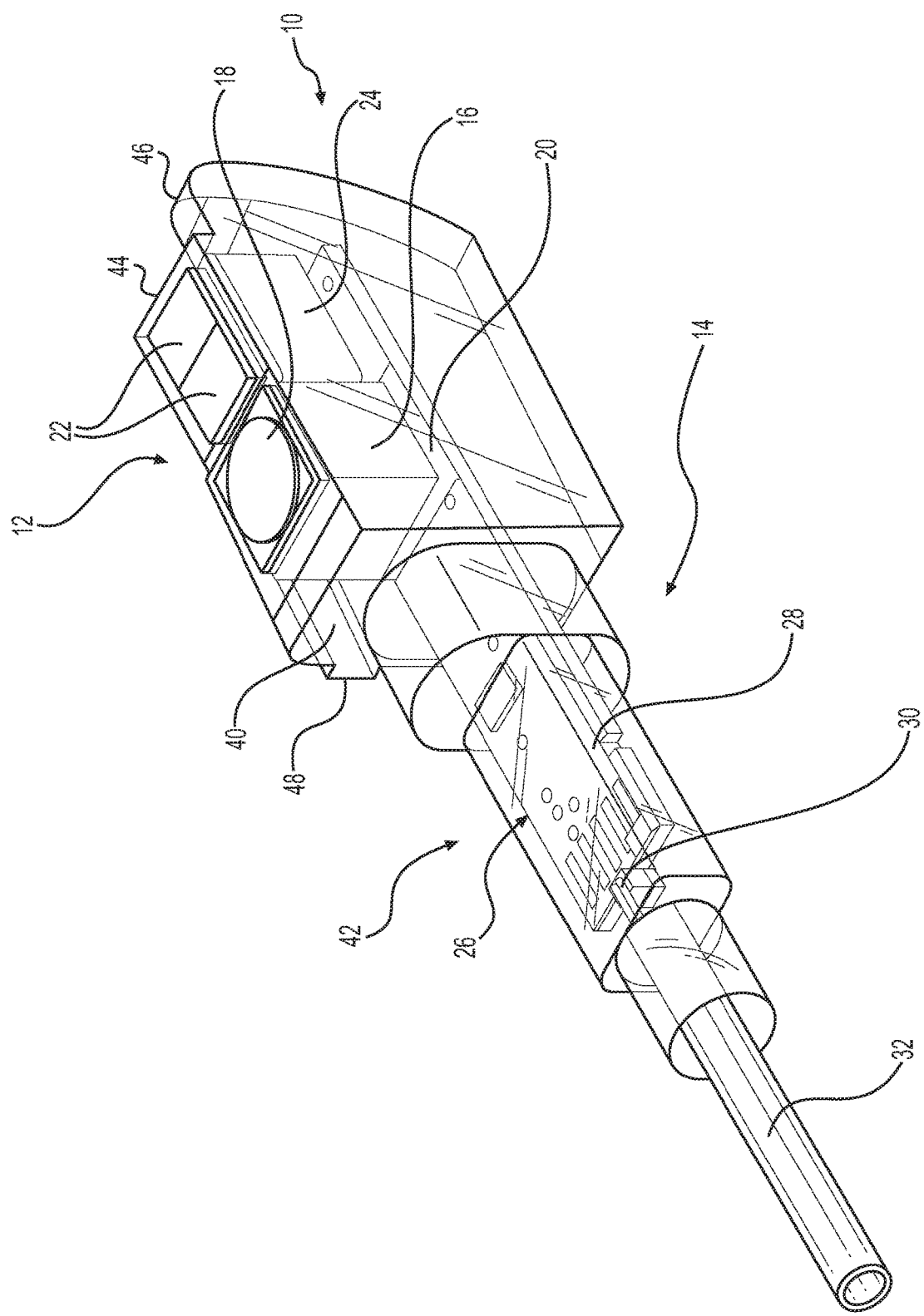
FIG. 1 depicts an exemplary encapsulated distal portion of a medical device.

FIG. 1 depicts an exemplary distal portion 10 of a medical device. Distal portion 10 may, for example, be used as a distal portion of an endoscope device. For example, distal portion 10 may be a distal end portion positioned at a distal end of an elongate insertable portion of an endoscope. Distal portion 10 may include, for example, one or more electronic components 12. The one or more electronic components 12 may be a portion of an electronics module 14. Electronics module 14 may include numerous electronic components 12. Electronic components 12 may be fixed together to form one electronics module 14, or certain of electronic components 12 may be separate, individual components.

Electronic components 12 may include, for example, an image capturing component, such as camera 16. Camera 16 may include, for example, one or more lenses 18, as well as an imager 20 and/or other imager-related circuitry. Camera 16 may also include other components, such as apertures, prisms, etc. Lenses 18 may serve to focus or otherwise manipulate light received from a location of interest (e.g., in a body lumen of a subject). Imager 20 may include electronic components which receive and/or process light received from a location of interest. Camera 16 may be an integrated module. In the alternative, camera 16 may include numerous separate components. Camera 16 may be capable of capturing still images and/or video. In the alternative to using a camera 16, distal portion 10 may include one or more lenses and/or light guides which serve to transmit images from a location of interest to a proximal end (e.g., a handle) of an endoscope.

Electronic components 12 of module 14 may also include one or more light sources, such as light emitting diodes (LEDs) 22. While the term LED may be used herein for convenience, it will be appreciated that any other light source may be used (e.g., optical fibers, lasers, or other mechanisms). Electronic components 12 may also include circuitry 24 for operating LEDs 22. Electronic components 12 may also, include, for example, sensors which are capable of sensing electromagnetic frequencies other than visible light. Electronic components 12 may also include mapping electronics including, for example, radio frequency (RF) sensors, accelerometers, and/or ultrasound sensors. Electronic components 12 may also include elements capable of creating and employing RF energy for therapeutic procedures.

Electronic components 12 of module 14 may further include circuitry 26, which may be operable to control one or more electronic components 12, such as camera 16 and/or LEDs 22. Circuitry 26 may include one or more circuit boards 28. Circuit board 28 may be a printed circuit board and may be a flexible, rigid, or semi-rigid circuit board. Portions of circuitry 26 may be connected to other electronic components carried in distal portion 10 or to components in a proximal controlling end of an endoscope (e.g., a handle or a controller) via, e.g. leads or wires. For example, wires 30 may provide a connection between electronic components 12 in distal portion 10, including circuit board 28, camera 16, and/or LEDs 22, and components in a proximal end of an endoscope (e.g., a handle). Wires 30 may be carried via a conduit 32, which may be, for example, tubular. Camera 16 and/or LEDs 22 may be mounted on circuit board 28.

Some or all of the electronic components 12 of module 14, as well as other components, may be provided in an encapsulation 40. Encapsulation 40 may be made of any suitable material. For example, encapsulation 40 may be made from a rigid material or a flexible material. Encapsulation 40 may be made from, for example, a plastic material and/or an epoxy. For example, encapsulation 40 may be made from a medical grade 2-part optically clear material (e.g., Loctite M-31CL or equivalent). Such a material may insulate heat producing electronics. A material such as an epoxy may be doped in order to dissipate or channel heat. For example, fine-powdered material with a high thermal conductivity (e.g., copper) could be blended into the material. Such a fine-powdered material may be blended so that it stays in suspension in an epoxy or other material forming encapsulation 40. In an alternative, encapsulation 40 may be formed using a low-pressure thermoplastic molding process using a viscous version/grade of polyamide (e.g., nylon) or other low temperature low viscosity thermoplastic, thermoset, or an ultraviolet light cured adhesive (e.g., Dymax 203A-CTH-F Multi-Cure). Encapsulation 40 may be made from a rigid epoxy as well as a pliable silicone. Encapsulation 40 could be formed so as to dissipate or insulate heat depending on design considerations related to use, subcomponent thermal generation properties, and/or recommended operating temperature limits of electronic components 12.

Encapsulation 40 may be made from a continuous or integral structure, which may include one or more materials. For example, encapsulation 40 may be molded (see, e.g., the discussion of FIG. 2, below). Encapsulation 40 may be, for example, an overmold. Encapsulation 40 may be formed of one monolithic material. In the alternative, encapsulation 40 may be formed from multiple materials, which may be mixed together, applied in layers, applied to different portions of distal tip 10, or otherwise applied. Even where multiple materials are used, encapsulation 40 may be continuous and may have no gaps between the different layers of material or may be continuous in that, even if gaps are left, the materials join to form one cohesive structure. Gaps in encapsulation 40 may not prevent it from having a continuous structure wherein the encapsulation 40 forms one cohesive unit or structure. Gaps may be filled with, for example, air or other fluids and/or other components, such as electronic components 12.

Encapsulation 40 may form a mechanically and electrically isolated shell and may be formed so as to include a wide variety of functional features, including mechanical and/or optical features, as discussed in further detail below. Encapsulation 40 may encompass electronic components 12, as discussed in further detail below. For example, encapsulation 40 may encompass all exposed surfaces of electronic components 12. Inner surfaces of encapsulation 40 may be mirror images the exposed exterior surfaces of electronic components 12. For example, referring to camera 16, encapsulation 40 may enclose and surround all surfaces or a subset of surfaces (such as side surfaces) of camera 16 and LEDs 22 that are not attached to other components such as circuit board 28. Encapsulation 40 may also fix electronic components 12 or other components of distal end 10 in place by fully embedding such components in encapsulation 40 and embeddedly fixing them in encapsulation 40. For example, encapsulation 40 may be allowed to harden so that it fills all crevices or other spaces between electronic components 12 or other components of distal end 10. Encapsulation 40 may be formed so that there is no space between an electronic component 12 and encapsulation 40. Encapsulation 40 may fixedly abut a surface of an electronic component 12, such as camera 16 and/or LEDs 22. For example, encapsulation 40 may fixedly abut a top and/or side surface of an electronic component 12, such as camera 16 and/or LEDs 22. It may or may not be the case that no other element, such as adhesive, may be present between encapsulation 40 and an abutting surface of an electronic component 12 such as a camera 16 and/or LEDs 22. Inner surfaces of encapsulation 40 may contact and at least partially encompass an electronic component 12 such as camera 16 and/or LEDs 22. For example, an inner surface of encapsulation 40 may be shaped so as to be a mirror image of shapes of exterior surfaces of electronic components 12 that contact the inner surfaces of encapsulation 40.

Encapsulation 40 may be formed from a transparent or translucent material so as to permit passage of light to or from electronic components 12 of distal portion 10, such as camera 16 and/or LEDs 22. In the alternative, portions of encapsulation 40 enclosing and/or surrounding electronic components 12 such as camera 16 and/or LEDs 22 may be formed from a transparent or translucent material, and other portions of encapsulation 40 may be formed from an opaque or partially opaque material.

All or portions of distal portion 10 may be housed within a cap portion (such as cap portion 440, as described below with regard to FIG. 5). For example, a cap portion may cover at least distal and side portions of distal portion 10. An exterior surface of encapsulation 40 may contact an interior surface of the cap portion. For example, an exterior surface of encapsulation 40 may have a shape that is a mirror image of an interior surface of the cap portion. A cap portion may be made of, for example, plastic. A cap portion may facilitate attachment of distal portion 10 to an elongate insertable portion of an endoscope. A cap portion may be glued or otherwise affixed to distal portion 10. Portions of encapsulation 40 and/or other components of distal portion 10 may form a connection portion 42, which may be used to connect distal portion 10 to other portions of an endoscope, such as a distal insertable portion of an endoscope. For example, a distal end of a medical device such as an endoscope may contain a receptacle for receiving connection portion 42. For example, inner surfaces of such a receptacle may be mirror images of exterior surfaces of connection portion 42. For example, distal portion 10 or a cap portion over distal portion 10 may be press-fit into a shaft (such as shaft 430, shown in FIG. 5) of an endoscope. Distal portion 10 may be secured to a distal insertable portion of an endoscope by glue, tape, an overmold, a sleeve, or any other securing mechanism, including mechanical locking. Connection portion 42 may have a smaller cross section than a distal portion of distal portion 10.

A cap portion may also include housings for features such as elevators, working channels, and outlets for air, water, and/or suction. Encapsulation 40 may be formed so as to mate with a cap portion. For example, a curved end portion 46 of encapsulation 40 may mate with a corresponding feature on a cap portion, and curved end portion 46 may aid in aligning, positioning, and/or connecting distal portion 10 with a cap portion or another component. Encapsulation 40 may also include, for example, a straight edge portion 44, which may mate with a complementary feature on a cap portion and aid in aligning, positioning, and/or connecting distal portion 10 with a cap portion or another component. Encapsulation 40 may also include a feature such as ridge 48, which may further mate with a cap portion or allow a press fit or a slide fit with a cap portion or with another portion of an endoscope or other device to which distal portion 10 is connected in order to aid in aligning, positioning, and/or connecting distal portion 10 with a cap portion or another component.

Figure 2:
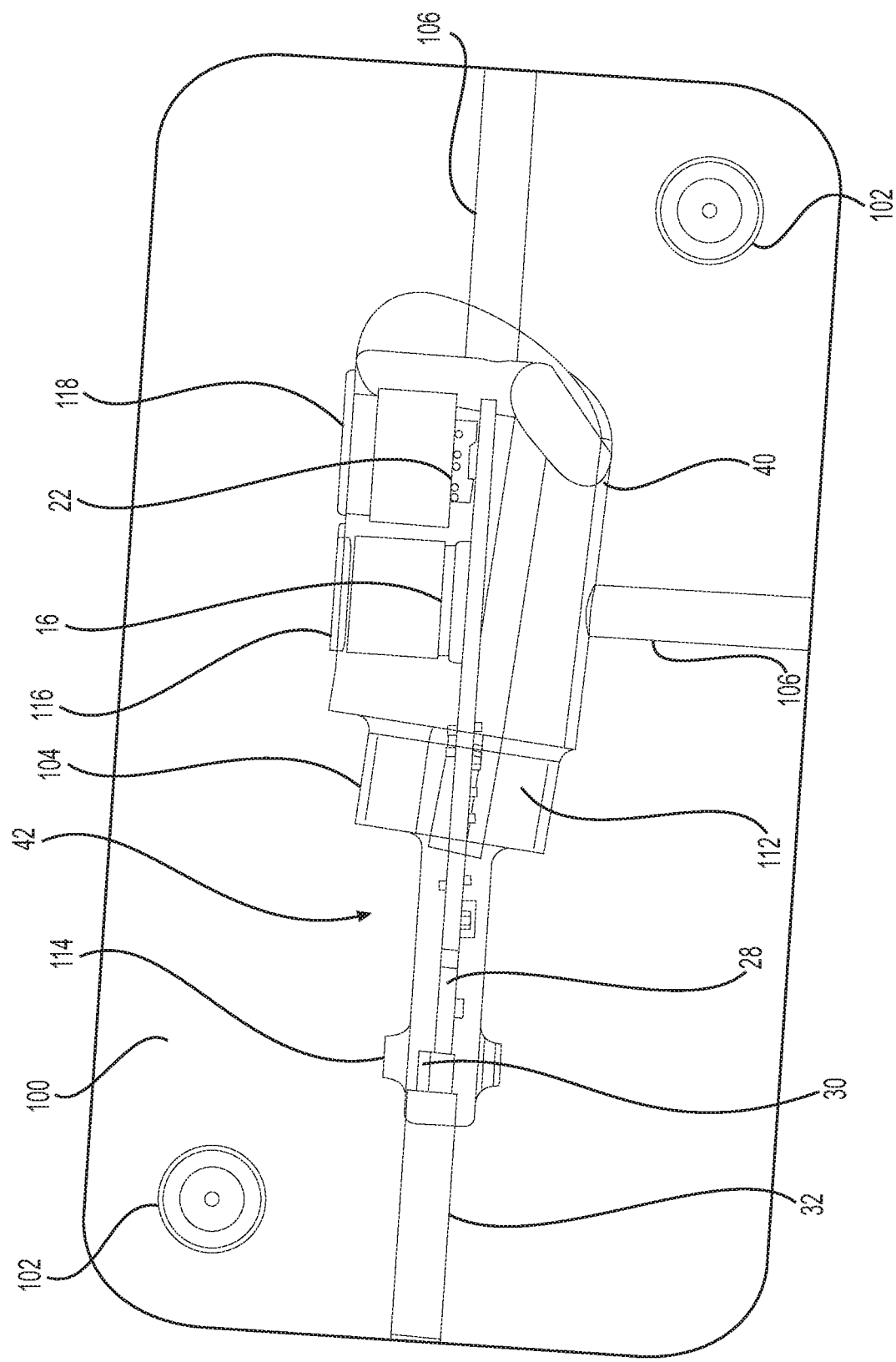
FIG. 2 depicts a cross-section of an exemplary mold for an encapsulated distal portion of a medical device.

FIG. 2 depicts a cross section of a distal portion 10 of an endoscope in a portion of a forming mold 100, which may be used to encapsulate electronic components module 14, including electronic components 12, and/or other components with encapsulation 40. Forming mold 100 may be made of any suitable material. For example, forming mold 100 may be formed from a low adhesion material such as silicone. In order to achieve encapsulation, module 14 and/or other components (such as electronic components 12 which are not joined in module 14) may be placed in forming mold 100. Forming mold 100 may include indicators (not shown) to assist in placement of module 14 in mold 100 prior to encapsulation. Module 14 may be placed in a first half (e.g., a bottom half) of forming mold 100. A second half of forming mold 100 (e.g., a top half) may then be put in place and may be snap fit to the first half using, for example, protrusions 102 in forming mold 100, or otherwise secured together via any suitable mechanical connection. For example, a first half of forming mold 100 may include protrusions 102, and a second half of forming mold 100 may include mirror-image indentations (not shown), in which protrusions 102 may be snap-fit. In the alternative, module 14 and/or other components (such as electronic components 12 which are not joined in module 14) may be placed in in any other kind of mold for the purpose of forming encapsulation 40.

Forming mold 100 may include a cavity 104 formed so as to be a negative version of desired encapsulation 40. Thus, when an encapsulating material is provided in forming mold 100 and the encapsulating material is hardened, encapsulation 40 will be formed. Forming mold 100 may also include one or more channels 106. Channels 106 may be used for injection of encapsulating material into cavity 104. In the alternative, any suitable method may be used for introducing encapsulating material into cavity 104.

Cavity 104 may be shaped so as to form mechanical features in encapsulation 40. For example, mechanical features of encapsulation 40 may aid in assembly of distal end 10 with other portions of an endoscope. For example, encapsulation 40 may include one or more flange portions 112, 114. Flange portions 112, 114 may aid in aligning, positioning, and/or connecting distal end 10 to a distal end of an insertable portion of an endoscope. Mechanical features of encapsulation 40 may also include, for example, snap-fit or other assembly aid-features. Such features of encapsulation 40 may be used to aid in placing distal end 10 into a cap or in attaching distal end 10 to an elongate insertion portion of an endoscope. For example, mechanical features of encapsulation 40 may include pins, notches, holes, grooves, and/or other features, such as pistons and/or cylinders, gears, racks, pulleys, sockets, and/or blocks and tackles, or combinations thereof. Mechanical features of encapsulation 40 may also include features such as fulcrums, wedges, and/or cams. For example, encapsulation 40 may include a curved end portion 46, a straight edge portion 40, and/or a ridge 48, as discussed above. Encapsulation 40 may also include flanges 112, 114, as discussed below with regard to FIG. 3A.

Encapsulation 40 may also include a camera covering 116 and/or an LED covering 118 which may cover top portions of camera 16 and/or LEDs 22, respectively. In the alternative, encapsulation 40 may lack camera covering 116 and and/or LED covering 118. Without such coverings 116, 118, portions of camera 16 and LEDs 22 may be exposed and outside of encapsulation 40. For example, encapsulation 40 may be formed without coverings 116, 118. Cavity 104 of forming mold 100 may lack the structure to form coverings 116, 118. In the alternative, portions of encapsulation 40 may be removed after molding of encapsulation 40 in forming mold 100. For example, portions of encapsulation 40 near optical components such as camera 16 and/or LEDs 22 may be removed after molding of encapsulation 40.

Forming mold 100 may be formed so as to tightly surround conduit 32. For example, conduit 32 may snap fit into forming mold 100 and encapsulating material may not flow around conduit 32, or only a thin layer of encapsulation material may be provided around conduit 32. In the alternative, conduit 32 may also be contained inside of encapsulation 40.

Distal portion 10 may also include, for example, a working channel, an end effector, an elevator, a suction port, or other features of a distal portion of an endoscope which are known or may become known. Such features may be formed from encapsulation 40 and/or other components, such as a cap portion. Where other components are used, they may be attached to distal portion 10 after forming encapsulation 40 or placed in mold 100 prior to forming encapsulation 40 so that they are integrated into encapsulation 40. Distal portion 10 may also be formed so as to include a solenoid for delivery and/or dispensing of drug agents or other media, such as contrast. Distal portion 10 and/or cavity 104 of mold 100 may also include sites for affixing mechanical villi to distal portion 10. Such mechanical villi may be used, for example, for steering or locomotion of one or more autonomous disposable devices through liquid media or cavities. Where such villi are used, distal portion 10 may be used as part of an autonomous device, rather than with an endoscope steerable by a physician or other user.

Encapsulation 40 may prevent ingress of water, bodily fluids, other liquids, or solid or gaseous materials into crevices or other portions of distal portion 10. For example, encapsulation 40 may protect electronic components 12 from damage due to liquids by being water tight, fluid tight, and/or liquid tight. Encapsulation 40 may also aid in sterilization of distal portion 10 by limiting the number of crevices where contaminants may be more difficult to remove. In addition or in the alternative, cost-effectiveness of producing distal portion 10, as well as other qualities of distal portion 10, may make it particularly suitable for incorporation into a sterilizable, biocompatible, single use device, which may reduce clinical risk and the cost of disinfection and re-sterilization. Distal portion 10 may be used in conjunction with an endoscope or other device to conduct a wide variety of medical procedures, including, for example, biopsy, ablation, ultrasound, placement of devices, or other diagnostic or therapeutic procedures.

A method for constructing distal end 10 may include placing or otherwise positioning or situating electronic components 12 (which may form a module 14) in a forming mold 100. Forming mold 100 may be injected with an encapsulation material made from, for example, plastic or epoxy or any of the other materials described above with regard to encapsulation 40, such as an ultraviolet light cured adhesive, a thermoplastic, and/or a thermoset. In the alternative to injection molding, any other encapsulation method may be used in order to encapsulate electronic components 12 with encapsulation material. For example, encapsulation material may be extruded in order to form encapsulation 40. Electronic components 12 may be encompassed by encapsulation 40. After an encapsulation material is introduced by use of a forming mold 10 or other mechanism, the encapsulation material may be allowed to cure or otherwise harden. Subsequently, an encapsulated distal end portion 10 may be removed from forming mold 100. Encapsulation may occur in multiple stages. For example, multiple molds may be used, or multiple layers of encapsulation material may otherwise be applied. As another example, different materials may be used in different portions of encapsulation 40, or materials may be mixed before, during, or after application to electronic components 12.

Use of the techniques described herein may reduce part count, the complexity of assembling the parts, and/or the cost of materials and manufacturing techniques. For example, molding of encapsulation 40 may be done efficiently at a high volume, whereas discrete machining operations of other techniques may be performed less efficiently. The techniques described herein may maintain equivalent functional performance of distal end 10 as compared to devices manufactured by other techniques.

Figure 3A:
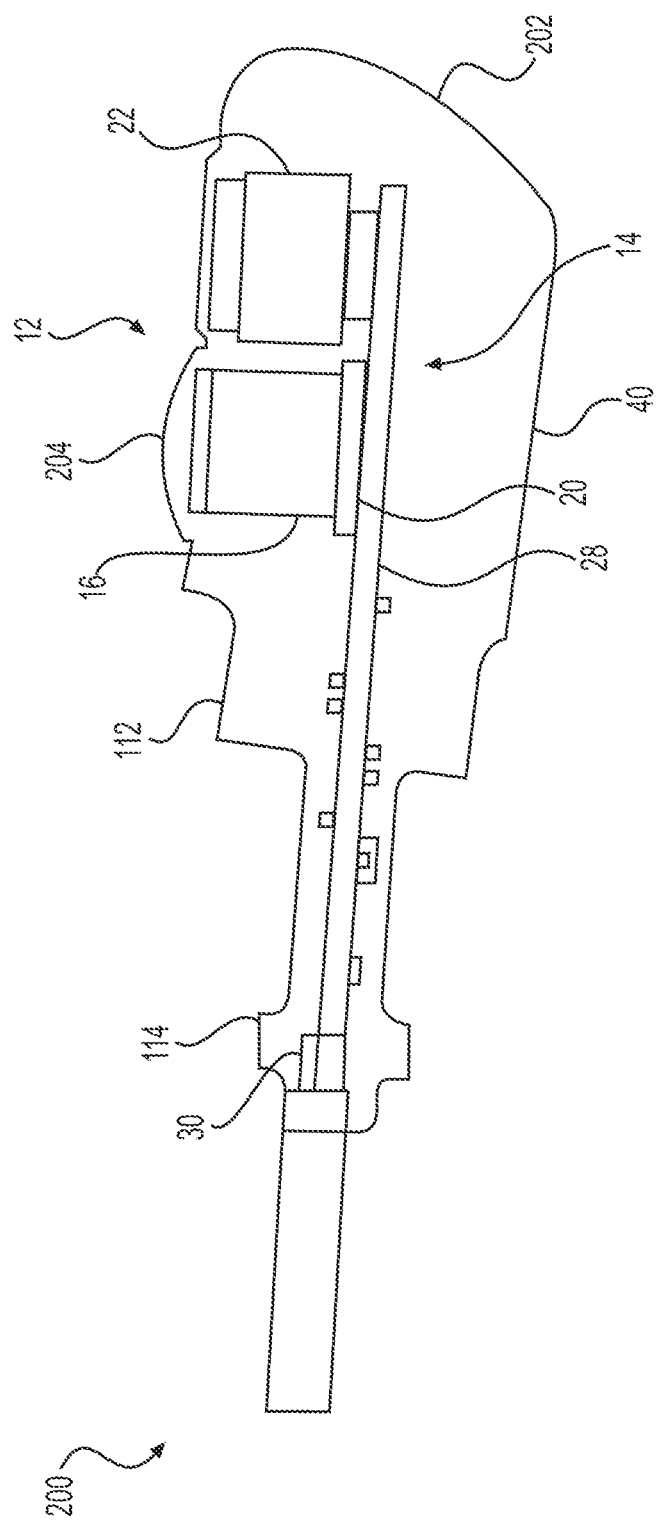
FIGS. 3A, 3B, and 4 depict exemplary encapsulated distal portions of an endoscope.
Figure 3B:
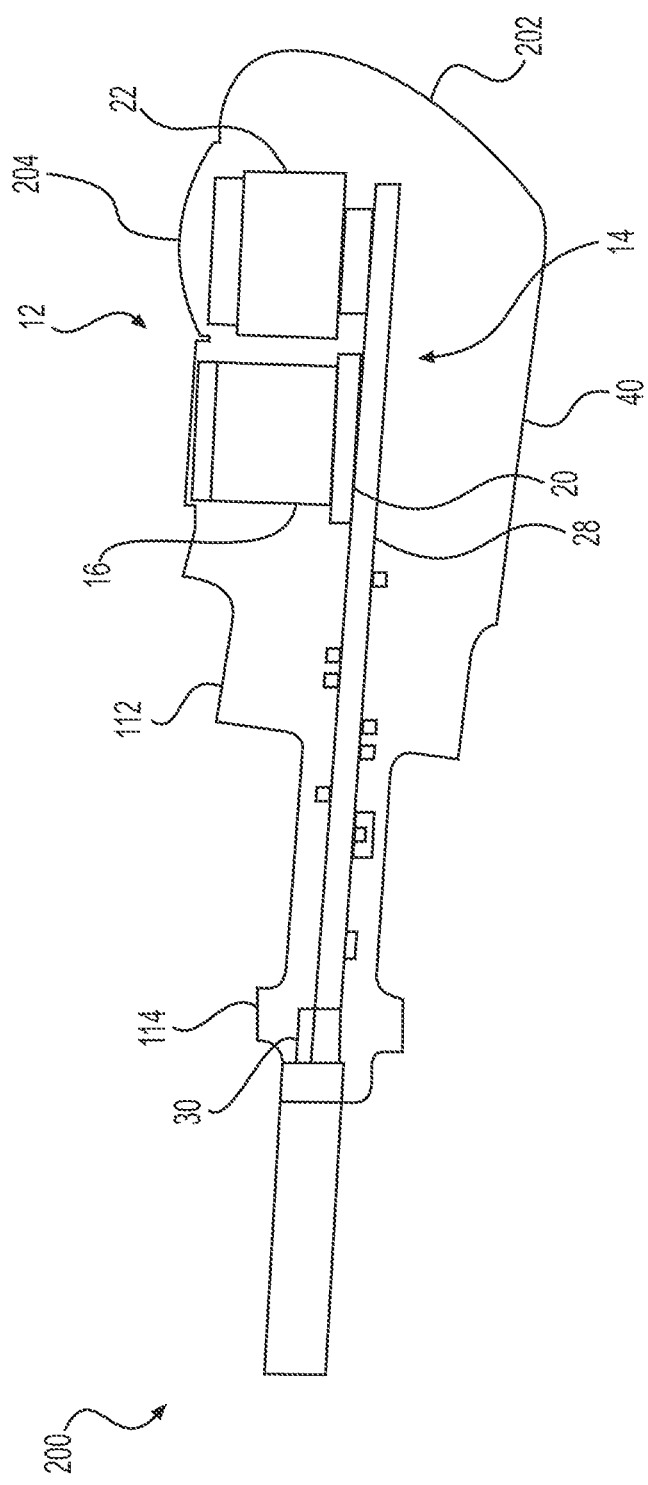

FIGS. 3A-3B show cross-sectional views of a distal end 200, which may be used as a distal end of an endoscope. Distal end 200 may have any of the properties of distal end 10, discussed above. Distal end 200 may be formed by a mold 100, according to, for example, the methods described above with regard to FIG. 2. Distal end 200 may include, for example, electronic components 12 such as one or more lenses and/or cameras 16 and/or one or more LEDs 22, as well as other electronic components 12 described above. Camera 16, LED 22, and/or other electronic components 12 (which may form an electronics module 14) may be encapsulated in encapsulation 40, which may be formed from any suitable encapsulation material, such as those discussed above with regard to FIGS. 1-2.

Encapsulation 40 may be formed into physical features which make distal end 200 compatible with a particular application. For example, a mold such as mold 100 may be formed with a cavity 104 that includes negatives of desired physical features of distal end 200. In the alternative, such physical features may be formed by removing material from encapsulation 40 after molding is completed. For example, encapsulation 40 may be formed so that distal end 200 may be used with a distal portion of an endoscope. Distal end 200, including encapsulation material 40, may have an elongate shape with respect to a longitudinal axis of distal end 200. A longitudinal axis of distal end 200 may be coaxial with or parallel to a longitudinal axis of an endoscope used in conjunction with distal end 200. Distal end 200 may also have features which provide a liquid tight, fluid tight, and/or water tight fit with a device such as an endoscope that does not allow ingress or egress of water or other fluids. For example, encapsulation 40 may be liquid tight and/or water tight and/or distal end 200 may be sealed to an endoscope. A portion of distal end 200 such as flange 112 or 114 may aid in positioning and/or securing distal end 200 to a device such as an endoscope and in establishing a seal between distal end 200 and an endoscope. In the alternative, flange 112 or 114 may aid in fitting an cap portion, as discussed above, on distal end 200. As a further example, distal end 200 may include a rounded distal portion 202 which may have atraumatic features and/or may be formed so as to fit in a complementary cap portion.

Encapsulation 40 may also include an optical feature 204 such as a lens. As with physical features of distal end 200 formed from encapsulation 40, optical feature 204 may be formed with a mold 100 having a cavity 104 including negatives of optical feature 204. In addition or in the alternative, optical feature 204 may be formed by techniques applied to encapsulation 40 after molding and/or curing of encapsulation 40. For example, portions of encapsulation 40 may be removed by mechanical or chemical methods. The curved shape of optical feature 204 shown in FIGS. 3A and 3B is merely exemplary. Optical feature 204 may be any number of shapes, including flat, convex, concave, or faceted.

While the term lens may be used herein to describe an exemplary optical feature 204, any light-modifying or other optical structure may be used. For example, optical feature 204 may be a prism and may, for example, split light into components with different polarizations. Optical feature 204 may also be any other refracting structure or a reflecting structure such as a mirror. It will be appreciated that the examples provided above are not intended to be limiting of the types of optical features 204 that may be used.

Optical feature 204 may be formed of the same encapsulation material which forms the remainder of encapsulation 40. In the alternative, optical feature 204 may be formed of a different encapsulation material than the material which forms the remainder of encapsulation 40. Optical feature 204 may also be formed by doping portions of encapsulation 40 with other materials either before or after molding and/or curing of encapsulation 40. Where a different material is used for optical feature 204, mold 100 may not need to be modified in order to form optical feature 204. Optical feature 204 may be undifferentiated in terms of shape from a remainder of distal portion 200. In the alternative, where a different material is used for optical feature 204, optical feature may also have a specialized shape formed by mold 100 during the molding process or by techniques applied after molding.

Optical feature 204 may have focusing properties and/or diffusing properties. As shown in FIG. 3A, optical feature 204 may serve to affect the light which enters camera 16 and is received by a processing component such as imager 20. Optical feature 204 may also be an aperture, filter, diffuser, a dispersing light feature, a mirror, a window, or a grating, or combinations thereof. Camera 16 may include additional lenses or other light-modifying features in addition to optical feature 204. In addition or in the alternative, as shown in FIG. 3B, optical feature 204 may serve to modify or otherwise affect light emitted by LED 22 or another structure. In addition or in the alternative, optical feature 204 may serve as a collimating and/or dispersing light feature. For example, optical feature 204 may serve to cause light rays emitted by LED 22 (or another light source) to be parallel or substantially parallel to one another. In an alternative, optical feature 204 may serve to cause light rays emitted by LED 22 (or another light source) to broaden or disperse.

Figure 4:
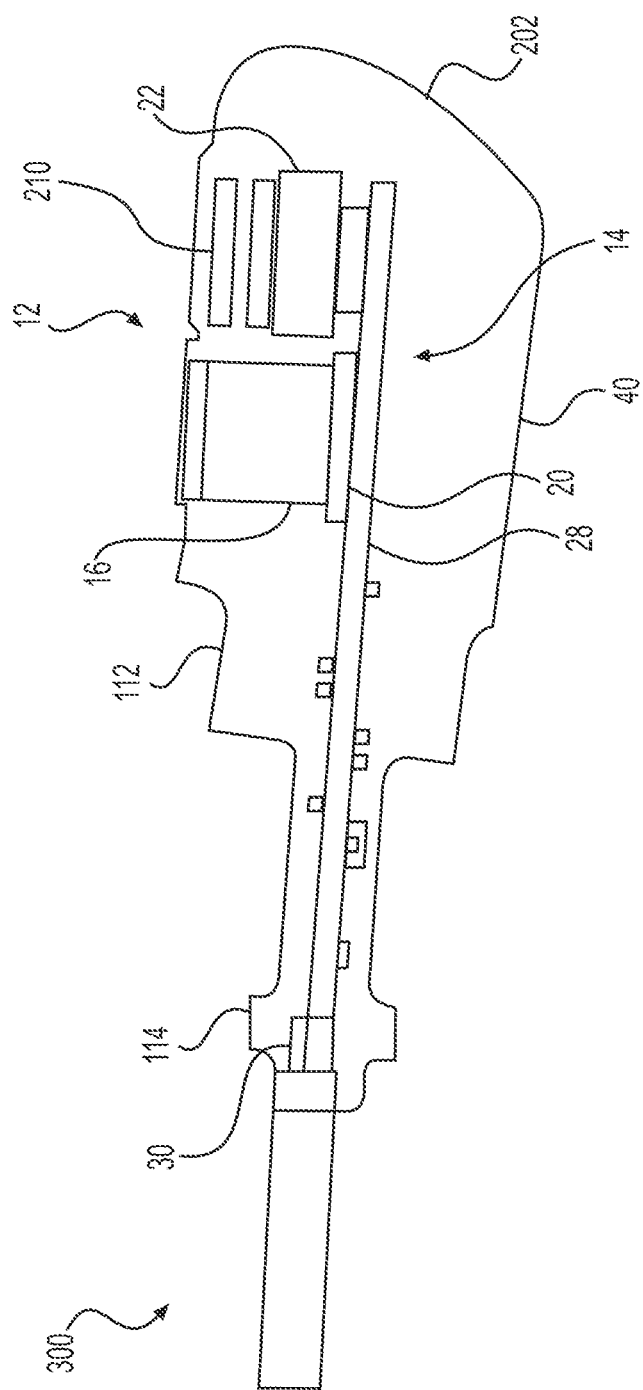

FIG. 4 shows a cross-sectional view of an exemplary distal end 300. Distal end 300 may include any of the features of distal ends 10 and/or 200, discussed above. Distal end 300 may also include a refracting feature 210. Refracting feature 210 may be embedded in encapsulation 40. For example, an inner surface of encapsulation 40 may contact an exterior surface of refracting feature 210. The inner surface of the encapsulation may be a mirror image of the exterior surface of refracting feature 210. Refracting feature 210 may be a separate element, or it may be a portion of encapsulation 40. For example, refracting feature 210 may be a doped portion of encapsulation 40. In the alternative, refracting feature 210 may be a separate component which may be placed in its desired location prior to forming encapsulation 40 from mold 100 or forming encapsulation 40 using any other known technique. As a further alternative, refracting feature 210 may be placed in its desired location in between two applications of encapsulation material. For example, encapsulation material may be used to form a first layer of encapsulation 40. Then, refracting feature 210 may be positioned on the first layer. Subsequently, further encapsulation material may be applied via, for example, a second mold, submersion, extrusion, or any other suitable technique.

Refracting feature 210 may be connected to an electrical current/voltage (e.g., via wires 30, circuitry 26, and/or circuit board 28). Refracting feature 210 may be operative to change properties upon application of an electric current or via another activating mechanism. For example, refracting feature 210 may change its levels of opacity and/or reflectance. Changes to refracting feature 210 (e.g., via a current) may result in differing refraction of light. For example, refracting feature 210 may be placed above LED 22 in order to cause refraction of light emitted from LED 22. In addition or in the alternative, refracting feature 210 may be placed above camera 16 in order to cause refraction of light reaching components of camera 16 (including, for example, imager 20).

Figure 5:
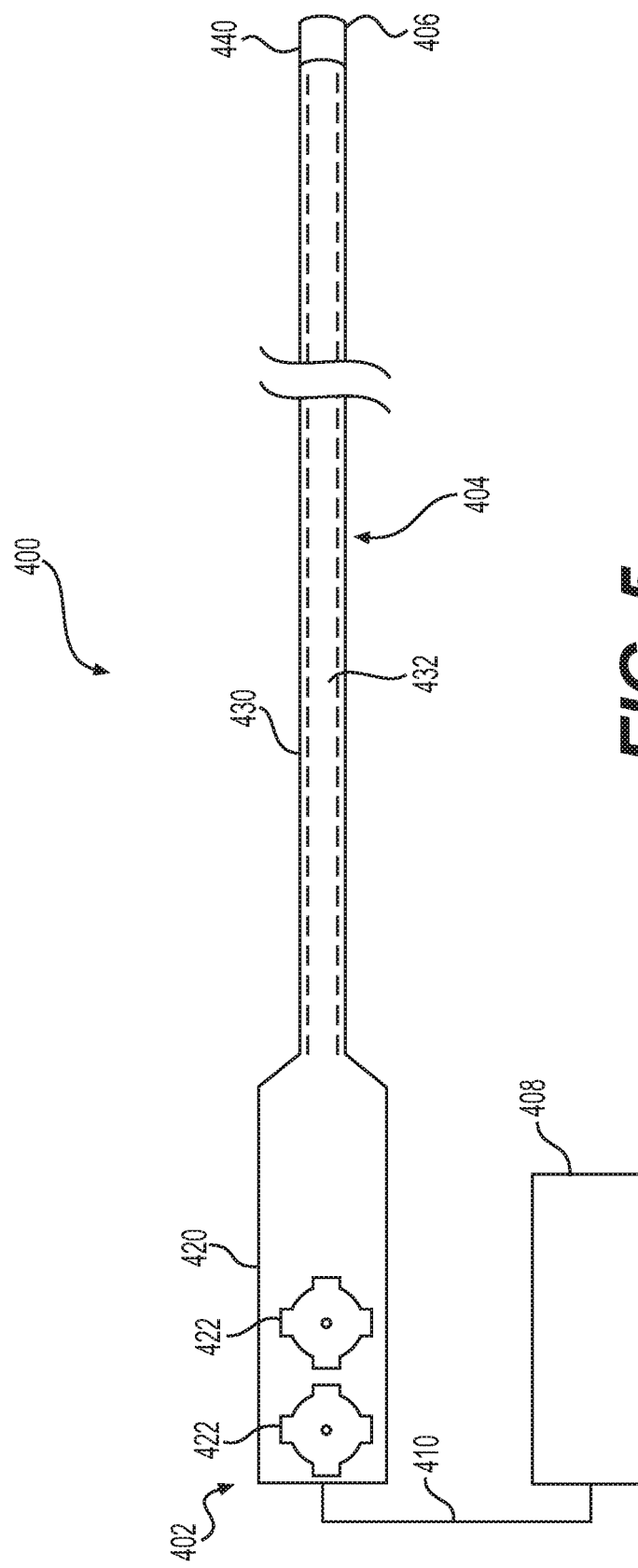
FIG. 5 depicts an exemplary endoscope.

FIG. 5 depicts an exemplary endoscope 400 having a proximal control portion 402, a distal insertable portion 404, and a distal end portion 406. Distal end portion 406 may have any of the qualities of distal end portions 10, 200, or 300, described above with regard to FIGS. 1-4. Endoscope 400 may be connected to a controller 408 via an umbilicus 410. Proximal control portion 402 may include a handle 420. Handle 420 may have one or more control mechanisms 422. Control mechanisms 422 may provide control over steering of insertable portion 404 or may allow for provision of air, water, suction, etc. Distal insertion portion 404 may include a shaft 430. Shaft 430 may have a lumen 432. Distal end portion 406 may include an encapsulation 40 (not shown) and any of the other features described above with regard to FIGS. 1-4. Distal end portion 406 may also include a cap portion 440. Distal end portion 406 may be fixedly or detachably attached to a portion of distal insertion portion 404 such as shaft 430.

Use of the techniques described herein may produce patient-insertable portions of medical devices which may be manufactured efficiently according to cost-effective methods. The encapsulation process described herein may allow for omission of manufacturing steps that require assembly of disparate components. Instead, the encapsulation process may serve to produce one integral member which need not be combined with other elements prior to attachment to a medical device such as an endoscope. Moreover, the resulting patient-insertable portion may be sealed against water, bodily fluids, and other liquids or fluids, as well as other potential contaminants. The techniques described herein may also permit further miniaturization of components of patient-insertable portions of medical devices and/or patient-insertable portions as a whole. For example, by integrating mechanical features (e.g., flanges 112, 114), optical features (e.g., optical feature 204 and/or refracting feature 210) into encapsulation 40, further miniaturization may be accomplished because those components no longer need to be manufactured as separate components which must be separately integrated.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A distal end portion of a medical device, the distal end portion having a proximal end and a distal end, the distal end portion comprising: an image capturing component including a lens, the lens including a side-facing surface between the proximal end and the distal end for receiving light from a first side of the distal end portion between the proximal end and the distal end; a light source including a light emitting diode (LED); and an encapsulation having inner surfaces contacting and at least partially encompassing the image capturing component and the light source, wherein a shape of the inner surfaces is a mirror image of a shape of exterior surfaces of the image capturing component and the light source that are contacted by the inner surfaces, wherein in a sagittal cross-section of the distal end portion that intersects the image capturing component and the LED there is an area between all surfaces of the image capturing component that face the LED and all surfaces of the LED that face the image capturing component, wherein the encapsulation fills all of the area, and wherein a distally facing surface of the encapsulation and the encompassed image capturing component and the light source includes only the encapsulation.

2. The distal end portion of claim 1, wherein the encapsulation forms a liquid tight shell.

3. The distal end portion of claim 1, wherein the encapsulation includes at least one of a prism, an aperture, a filter, a diffuser, a dispersing light feature, a mirror, a window, a grating, or a collimating light feature, or combinations thereof.

4. The distal end portion of claim 1, further comprising a circuit board, wherein the inner surfaces of the encapsulation contact and at least partially encompass the circuit board, wherein a shape of the inner surfaces is a mirror image of a shape of exterior surfaces of the circuit board.

5. The distal end portion of claim 4, wherein:
the inner surfaces of the encapsulation contact at least a side surface of the image capturing component;
the inner surfaces of the encapsulation contact at least a top surface and at least a side surface of the light source; and
the inner surfaces of the encapsulation contact at least a bottom surface of the circuit board.

6. The distal end portion of claim 1, further comprising a layer configured to change opacity or reflectance when an electrical current or voltage is applied to the layer.

7. The distal end portion of claim 1, further comprising a cap portion, wherein:
the encapsulation is formed from a molded, monolithic material;
the inner surfaces of the encapsulation contact at least a side surface of the image capturing component;
the inner surfaces of the encapsulation contact at least a top surface and at least a side surface of the light source; and
exterior surfaces of the encapsulation contact inner surfaces of the cap portion.

8. The distal end portion of claim 7, wherein the encapsulation includes a ridge shaped so as to mate with the cap portion, wherein the ridge includes a side-facing surface between the proximal end and the distal end of the distal end portion, protruding from an adjacent surface of the encapsulation, and defining a linear edge, for aligning the encapsulation with the cap portion and permitting a slide fit or a press fit between the encapsulation and the cap portion.

9. A method for forming a distal end portion of a medical device, comprising:
positioning only an image capturing component, a light source, a conduit, and circuitry associated with the image capturing component and the light source in a cavity of a mold, wherein the image capturing component includes a lens, and the lens of the image capturing component includes a side-facing surface between a proximal end of the distal end portion and a distal end of the distal end portion for receiving light from a side of the distal end portion between the proximal end and the distal end;

introducing an encapsulating material into the cavity, wherein the introduced encapsulating material encompasses at least a portion of the image capturing component and a portion of the light source;

allowing the encapsulating material to harden;

removing the distal end portion from the mold; and attaching the distal end portion to a distal end of a shaft to form an endoscope, wherein the endoscope comprises a proximal control portion at a proximal end of the shaft, wherein the shaft and the distal end portion are configured for insertion into a body lumen of a patient while the proximal control portion remains outside the body lumen.

10. The method of claim 9, wherein the cavity includes a negative of at least one of a prism, an aperture, a filter, a diffuser, a dispersing light feature, mirror, a window, a grating, or a collimating light feature, or combinations thereof.

11. The method of claim 9, wherein the circuitry includes a circuit board, wherein the introduced encapsulating material encompasses at least a portion of the circuit board, wherein the light source includes a light emitting diode (LED), wherein in a sagittal cross-section of the distal end portion that intersects the image capturing component and the LED there is an area between all surfaces of the image capturing component that face the LED and all surfaces of the LED that face the image capturing component, and wherein the encapsulation fills all of the area.

12. The method of claim 11, wherein the cavity includes a negative of a flange of the encapsulation, wherein the flange includes a side-facing surface between the proximal end and the distal end of the distal end portion, and the flange is shaped so as to mate with the distal end of the shaft and, upon attaching the distal end portion to the distal end of the shaft, establish a seal between the shaft and the distal end portion.

13. A medical device, comprising: a longitudinal axis extending from a distal end of the medical device to a proximal end of the medical device, wherein the medical device is an endoscope; a proximal control portion; a distal insertion portion attached to a distal end of the proximal control portion, wherein the distal insertion portion is configured for insertion into a body lumen of a patient while the proximal control portion remains outside the body lumen; and a distal end portion attached to a distal end of the distal insertion portion, wherein the distal end portion comprises a component and an encapsulation, wherein the component includes (1) a light source including a light emitting diode (LED) and (2) an image capturing component, wherein the image capturing component includes a lens, the lens including a side-facing surface between a proximal of the distal end portion and a distal end of the distal end portion, for receiving light from a first side of the distal end portion between the proximal end of the distal end portion and the distal end of the distal end portion, wherein the encapsulation includes a first portion and a second portion adjacent to and proximal to the first portion, wherein in a sagittal cross-section of the distal end portion that intersects the image capturing component and the LED there is an area between all surfaces of the image capturing component that face the LED and all surfaces of the LED that face the image capturing component, wherein the encapsulation fills all of the area, wherein a largest cross-sectional dimension of the first portion of the encapsulation measured perpendicular to the longitudinal axis is greater than a largest cross-sectional dimension of the second portion of the encapsulation measured perpendicular to the longitudinal axis, wherein the encapsulation has inner surfaces contacting and at least partially encompassing the component, and wherein a shape of the inner surfaces is a mirror image of a shape of exterior surfaces of the component that are contacted by the inner surfaces.

14. The medical device of claim 13, wherein the encapsulation forms a liquid tight shell.

15. The medical device of claim 13, wherein the encapsulation includes at least one of a prism, an aperture, a filter, a diffuser, a dispersing light feature, mirror, a window, a grating, or a collimating light feature, or combinations thereof.

16. The medical device of claim 13, further comprising: a cap portion, wherein the inner surfaces of the encapsulation contact at least a top surface and at least a side surface of the component, wherein exterior surfaces of the encapsulation contact inner surfaces of the cap portion, wherein the exterior surfaces include: (1) a ridge protruding from an adjacent surface of the encapsulation, including a side-facing surface between a proximal end and a distal end of the distal end portion, and defining a linear edge for aligning the encapsulation with the cap portion and permitting a slide fit or a press fit between the encapsulation and the cap portion; and (2) a distally-facing curved surface at a distal-most end of the encapsulation, and wherein the distally-facing curved surface protrudes from adjacent surfaces of the encapsulation and mates with a corresponding feature of the cap portion.

17. The distal end portion of claim 7, wherein the encapsulation comprises a distally-facing curved surface at a distal-most end of the encapsulation, wherein the distally-facing curved surface protrudes from adjacent surfaces of the encapsulation and mates with a corresponding feature of the cap portion.

18. The method of claim 9, wherein the encapsulation comprises a distally-facing curved surface at a distal-most end of the encapsulation, wherein the distally-facing curved surface protrudes from adjacent surfaces of the encapsulation and mates with a corresponding feature of a cap portion.

19. The medical device of claim 13, wherein the encapsulation includes a third portion adjacent to and proximal to the second portion, and wherein the largest cross-sectional dimension of the second portion measured perpendicular to the longitudinal axis is greater than a largest cross-sectional dimension of the third portion measured perpendicular to the longitudinal axis.

20. The medical device of claim 19, wherein the encapsulation includes a fourth portion adjacent to and proximal to the third portion, and wherein the largest cross-sectional dimension of the third portion measured perpendicular to the longitudinal axis is greater than a largest cross-sectional dimension of the fourth portion measured perpendicular to the longitudinal axis.

* * * * *